United States Patent [19]

Cereda et al.

[11] Patent Number: 5,164,386
[45] Date of Patent: Nov. 17, 1992

[54] R(−)3-QUINUCLIDINOL DERIVATIVES

[75] Inventors: Enzo Cereda, Tortona; Giuseppe Bietti, Milan; Giovanni B. Schiavi, Asola; Arturo Donetti, Milan; Antonio Schiavone, Trezzano, all of Italy; Henri N. Doods, Warthausen, Fed. Rep. of Germany

[73] Assignee: Istituto de Angeli S.p.A., Milan, Italy

[21] Appl. No.: 541,106

[22] Filed: Jun. 20, 1990

[30] Foreign Application Priority Data

Jun. 20, 1989 [IT] Italy .................. 20929 A/89

[51] Int. Cl.$^5$ .................. A61K 31/55; A61K 31/44; C07D 453/02
[52] U.S. Cl. .................. 514/212; 514/305; 540/524; 546/137
[58] Field of Search .......... 540/524; 546/137; 514/212, 305

[56] References Cited

U.S. PATENT DOCUMENTS

| | | | |
|---|---|---|---|
| 3,290,316 | 12/1966 | Stempel | 546/137 X |
| 4,921,982 | 5/1990 | Cohen et al. | 546/137 X |
| 4,975,437 | 12/1990 | Carter et al. | 546/137 X |

*Primary Examiner*—Marianne M. Cintins
*Assistant Examiner*—Catherine Scalzo
*Attorney, Agent, or Firm*—David E. Frankhouser; Alan R. Stempel; Mary-Ellen M. Timbers

[57] ABSTRACT

Pharmacologically active R(−) 3-quinuclidinol derivatives are described which are muscarinic receptor blocking agents useful for the treatment of gastrointestinal and respiratory tract disorders of the following formula (I)

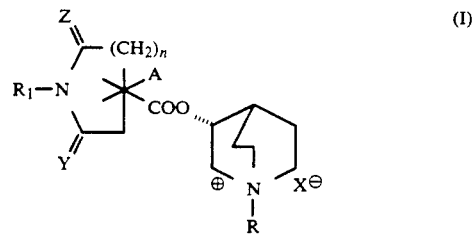

wherein
R represents a linear or branched lower alkyl group, a cycloalkyl-$C_{1-2}$ alkyl or an aralkyl group, or it is absent;
X represents the anion of an organic or inorganic acid, or it is absent, when R is absent;
$R_1$ represents H, a linear or branched lower alkyl group or an acyl group of the type $R_2$—CO, in which $R_2$ is H or a linear or branched lower alkyl group;
A represents a cycloalkyl, an aromatic ring or a 5- or 6-membered heterocyclic ring;
Y and Z may be simultaneously or alternatively present or absent; when they are simultaneously present, they represent oxygen; when only one of them is present, it is oxygen or sulphur;
n is 1, 2 or 3;
A and the 3-quinuclidinyl ester groups are inserted simultaneously on the same carbon atom of the ring to give rise to a geminal substitution.

The process for the preparation of the compounds of formula (I) as well as pharmaceutical compositions containing them are also described.

9 Claims, No Drawings

R(—)3-QUINUCLIDINOL DERIVATIVES

The present invention relates to novel pharmacologically active R(—) 3-quinuclidinol derivatives, to the process for their preparation and to the pharmaceutical compositions containing them. The new compounds are muscarinic receptor blocking agents and may be used for the prevention and the treatment of the gastrointestinal and respiratory tract disorders arising from an overstimulation of the muscarinic receptors.

It is known that administration of muscarinic receptor blocking agents, gives rise to a number of pharmacological effects like decreased gastrointestinal motility, inhibition of acid secretion, bronchodilation, dry mouth, mydriasis, urinary retention, decreased sweating, tachycardia. Furthermore, antimuscarinic agents with tertiary amine structures may give rise to central effects owing to their penetration across blood-brain barrier. The lack of selectivity among these actions makes it difficult to address therapy in one specific indication and this prompted chemical modification of these agents. A major improvement in this sense was achieved with the discovery of Pirenzepine which is able to bind with high affinity to the muscarinic receptors ($M_1$ type) located in neuronal tissues (brain, ganglia), in the enteric nervous system and in lung tissues; nowadays Pirenzepine is therapeutically used as an antisecretory and antiulcer agent [R. Hammer et al.-Nature 283, 90, 1980; N. J. M. Birdsall et al.—Scand. J. Gastroenterol.: 15, (Suppl. 66) 1, 1980]. Moreover its use in the treatment of bronchoconstriction has been claimed (Pat. Appln. WO 8608 278). The receptors with low affinity to Pirenzepine ($M_2$ type), present mainly but not exclusively, in effector organs were further subdivided according to the different abilities of selected antagonists in inhibiting the muscarinic responses in tissue preparations such as guinea pig longitudinal ileum and guinea pig paced left atrial [R. B. Barlow et al.—British J. Pharmacol. 89, 837 (1986); R. Micheletti et al.—J. Pharmacol. Exp. Ther. 241, 628 (1987); R. B. Barlow et al. British J. Pharmacol. 58, 613 (1976)]. The compound AF-DX-116 (11-2-{[2-(diethylamino)methyl-1-piperidin-yl]acetyl}-5,11-dihydro-6H-pyrido-(2,3-b)(1,4)benzodiazepin-6-one) may be considered the prototype of cardioselective compounds, whereas 4-DAMP (4-diphenylacetoxy-N-methylpiperidine methobromide) is the prototype of smooth muscle selective compounds.

We have now synthetized, and this is the object of the present invention, a new class of R(—) 3-quinuclidinol derivatives which possess a good affinity and selectivity for the $M_1$ receptors, in comparison with $M_2$ receptors.

Moreover, unlike Pirenzepine, these novel compounds are able to antagonize potently and selectively the functional muscarinic responses in selected smooth muscle. The novel compounds may therefore be used in the treatment of gastrointestinal disorders such as peptic ulcer disease, irritable bowel syndrome, spastic constipation, cardiospasm, pylorospasm without concomitant effects on heart rate and without other atropine-like side-effects.

The compounds, object of the present invention, may be also used in the treatment of obstructive acute and chronic spastic disorders of the respiratory tract, such as bronchoconstriction, chronic bronchitis, emphysema and asthma without atropine-like side-effects particularly on the heart.

Furthermore they may be used in the treatment of the spasms of the urinary and biliary tracts and in the treatment of urinary incontinence. According to the present invention we provide compounds of general formula (I)

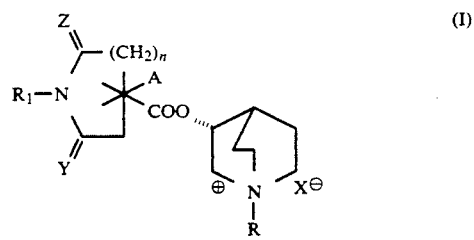

wherein

R represents a linear or branched lower alkyl group, a cycloalkyl-$C_{1-2}$alkyl or an aralkyl group, or it is absent;

X represents the anion of an organic or inorganic acid, or it is absent, when R is absent;

$R_1$ represents H, a linear or branched lower alkyl group or an acyl group of the type $R_2$—CO, in which $R_2$ is H or a linear or branced lower alkyl group;

A represents a cycloalkyl, an aromatic ring or a 5- or 6-membered heterocyclic ring;

Y and Z may be simultaneously or alternatively present or absent; when they are simultaneously present, they represent oxygen; when only one of them is present, it is oxygen or sulphur;

n is 1, 2 or 3;

A and the 3-quinuclidinyl ester groups are inserted simultaneously on the same carbon atom of the ring to give rise to a geminal substitution. For pharmaceutical use the compounds of general formula (I), when R and X are absent, may be used as such or in the form of physiologically compatible acid addition salts thereof. The term "acid addition salts" includes salts either with inorganic or organic acids. Physiologically compatible acids which may be used in salt formation include, for example, maleic, citric, hydrochloric, tartaric, hydrobromic, fumaric, nitric, sulfuric, methanesulfonic or hydroiodic acid.

When in the compounds of general formula (I) R, $R_1$ and $R_2$ represent a linear or branched lower alkyl group these may, for example, be alkyl groups containing from 1 to 3 carbon atoms. When A represents a cycloalkyl group, it may, for example, contain from 5 to 7 carbon atoms; when A represents an aromatic ring, it may, for example, be a phenyl ring. When A represents a 5- or 6-membered heterocyclic ring, it may, for example, be thiophene, pyridine or piperidine. When X represents the anion of an organic or inorganic acid, it may, for example, be Cl, Br, I or $CH_3SO_4$.

It has to be understood that, in the above mentioned compounds of formula (I), A and the 3-quinuclidinyl ester groups may be inserted in any position of the ring free for the substitution and they are always inserted together on the same carbon atom to give rise to a geminal substitution. The compounds of formula (I), according to the present invention, possess a second chiral centre which is represented by the carbon atom to which the geminal substituents A and 3-quinuclidinyl ester are bound, and therefore they may be in the form of mixture of two diastereoisomers, which are within the scope of the invention itself.

It is to be understood that, when mixtures of diastereoisomers are present, they may be separated into the pure single components according to the classical resolution methods based on their different physical chemical properties e.g. by fractional crystallization or by chromatographic separation with a suitable mixture of solvents. Therefore also the single components of the diastereoisomeric mixture and their use in the prevention and in the treatment of the previously mentioned gastrointestinal, respiratory, urinary or biliary tract disorders are within the scope of the present invention.

A preferred group of compounds according to the present invention is the one formed by the compounds of general formula (I) wherein $R_1$ is H, Z is oxygen or sulphur, n is 1, 2 or 3 and A is a phenyl or thiophene ring, R is absent or it is a linear or branched lower alkyl or a cycloalkyl-$C_{1-2}$ alkyl group, X is absent or it is halogen. Such compounds have a good affinity for $M_1$ muscarinic receptor subtypes.

The compounds of general formula (I) may, for example, be prepared by the following process which constitutes a further feature of the present invention.

Compounds of general formula (I) in which R and X are absent and A, Y, Z, $R_1$ and n are as hereinbefore defined, may be obtained by reacting $R(-)$ 3-quinuclidinol with a reactive derivative of a carboxylic acid of formula (II)

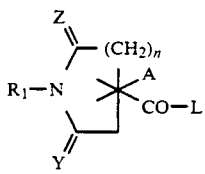
(II)

in which $R_1$, Z, Y, n and A are as hereinbefore defined and L represents a suitable leaving group. Suitable leaving groups are halogens, lower alkoxy groups, phenoxy groups, imidazol-1-yl, ethylcarbonyldioxy, mesiloxy and (benzotriazol-1-yl)oxy, preferably chlorine, ethoxy, imidazol-1-yl. The yields of the process can be conveniently improved by adding to the reaction mixture basic substances as catalysts such as Na pieces, NaH, 4-dimethylaminopyridine (DMAP), $NEt_3$, 1,8diazabicyclo[5.4.0]undec-7-ene (DBU) or pyridine. The reaction is carried out in an anhydrous inert solvent selected from dichloromethane, chloroform, benzene, toluene, etylacetate, THF, DMF or a mixture of them. The reaction temperature is generally kept between 0° and 100° C., preferably at 50° C.

The intermediates of formula (II), when L is a lower alkoxy group, used as starting material in the above described process, are obtained according to already known procedures [Arch. Pharmazie 314, 657, 1981; J. Am. Chem. Soc. 81, 737, 1959; J. Chem. Soc. (c) 802, 1966], or in the case of new intermediates by allowing an amino derivative of formula (III)

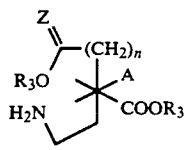
(III)

wherein A, Z and n are as above defined and $R_3$ is a lower $C_{1-3}$alkyl group, to cyclize intramolecularly. The cyclization reaction is carried out in the absence or in the presence of an inert solvent, preferably selected from diethyl ether, benzene or ethylacetate at a temperature between 0° C. and the boiling point of the solvent, preferably at room temperature.

The intermediates of formula (II), when L is different from lower alkoxy groups, may be obtained by hydrolizing a cyclic ester of formula (II), in which L is a lower alkoxy group, to the corresponding carboxylic acid and by converting them into the other listed reactive derivatives as above mentioned.

The intermediate amine of formula (III) may be prepared by reducing a cyano derivative of formula (IV) or by deprotecting a masked amino group in a compound of formula (V)

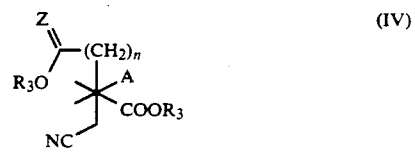
(IV)

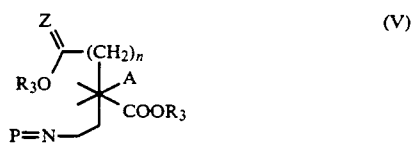
(V)

in which Z, $R_3$, n and A are as herein before defined and P represents a suitable amino protecting group such as a benzylidene or a phthaloyl group. The reduction process is carried out according to conventional methods, for example by hydrogenating a compound of formula IV in the presence of C/Pd, Raney/Ni, Ru/C as catalysts, preferably Raney/Ni.

Methanol, ethanol, ethylacetate and 2-propanol are the preferred solvents; the pressure may range from 1 to 5 Atm, preferably 1 Atm. The deprotection of compounds of formula (V) may be carried out according to well established procedures such as by reacting them with hydrazine hydrate in an alcoholic solvent or with a diluted hydrochloric acid aqueous solution.

Compounds of formula (IV) and (V) are conveniently prepared by reacting a compound of formula (VI)

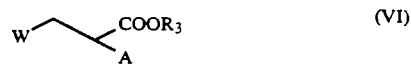
(VI)

in which A and $R_3$ are as hereinbefore defined and W represents a cyano or a P=N- groupment, in which P is as hereinbefore defined, with a reactive halogen derivative of formula (VII)

(VII)

in which Hal represents chlorine or bromine atoms and n, Z and $R_3$ are as previously defined. This process is carried out in the presence of a strong base, such as EtONa, MetONa, NaH, K-t-butylate, in a polar solvent such as EtOH, MetOH, DMF or toluene at a temperature between 15° and 100° C., preferably at room temperature.

In some particular cases intermediate compounds of formula (II), in which $R_1$ is a linear or branched lower alkyl group or an acyl group of the type $R_2$—CO, may be conveniently prepared by alkylating or acylating a compound of formula (VIII)

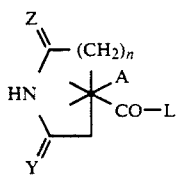

in which Z, Y, n, A and L are as hereinbefore defined, with a linear or branched lower alkyl halide or with an acyl halide such as R₂COCl in the presence of MetONa, NaH, pyridine or NEt₃. The process is carried out utilizing DMF, benzene, toluene, THF, CH₂Cl₂ or ethylacetate as a solvent at a temperature ranging from 15° to 130° C., preferably at room temperature.

In another particular case, when in the compounds of formula (II) Y is absent and Z represents a sulfur atom and $R_1$, n, A and L are as hereinbefore defined, they may be prepared by reacting an intermediate compound of formula (IX)

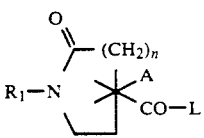

in which $R_1$, n, A and L are as hereinbefore defined, with a sulphurization agent such as $P_2S_5$ or the Lawesson's reagent [2.4-bis-(4-methoxyphenyl)-2-4-dithioxo-1,3,2,4-dithiadiphosphetane]. The solvent for this process is selected from benzene, toluene or DMF at a temperature between 40° C. and 130° C., preferably at 80° C.

When in the compounds of formula (I) R and X are present, they can be prepared by reacting the compounds of formula (I), in which R and X are absent and Z, Y, $R_1$, n and A are as hereinbefore defined, in a conventional manner with an alkylating agent such as a linear or branched lower alkyl halide, a cycloalkyl-$C_{1-2}$alkyl halide, an aralkylhalide or dimethylsulfate preferably methylbromide, cyclopropylmethyl bromide, dimethylsulfate. The reaction is carried out in a polar solvent selected from acetonitrile, methanol, ethanol, preferably acetonitrile, at a temperature ranging from 30° to 70° C., preferably at 50° C.

The compounds of general formula (I), in which R and X are absent and prepared according to the above described process, may be, if desired, converted into the corresponding physiologically compatible acid addition salts with an inorganic or organic acid, for example, by conventional methods such as by reacting the compounds as bases with a solution of the corresponding acid in a suitable solvent. Particularly preferred acids include for example hydrochloric, hydrobromic, sulfuric, methanesulfonic or tartaric acid.

Particulaly preferred compounds, according to the present invention, are the following:

Pyrrolidine-2-oxo-4-phenyl-4[(R)-1-azabicyclo(2.2.2)-octyl]-carboxylate (compound 2)
Piperidine-2,6-dioxo-3-phenyl-3-[(R)-1-azabicyclo(2.2.2)-octyl]-carboxylate (compound 4)
Piperidine-2-oxo-6-phenyl-6-[(R)-1-azabicyclo(2.2.2)-octyl]-carboxylate (compound 5)
Pyrrolidine-2-oxo-5-phenyl-5-[(R)-1-azabicyclo(2.2.2)-octyl]-carboxylate (compound 6)
Azepine-2-oxo-6-phenyl-6-[(R)-1-azabicyclo(2.2.2)-octyl]-carboxylate, single diastereoisomer (compound 11)
Azepine-2-oxo-6-phenyl-6-[(R)-1-azabicyclo(2.2.2)-octyl]-carboxylate, single diastereoisomer (compound 12)
Piperidine-2-oxo-3-phenyl-3-[(R)-1-azabicyclo(2.2.2)-octyl]-carboxylate (compound 19)
Piperidine-2-oxo-5-phenyl-5-[(R)-1-azabicyclo(2.2.2)-octyl]-carboxylate (compound 20)

As already mentioned hereinbefore, the new compounds of formula (I) according to the present invention have interesting pharmacological properties owing to their ability to antagonize the physiological muscarinic effects in warm blooded animals.

Therefore the new compounds are therapeutically useful in the prevention or in the treatment of disorders wherein muscarinic receptors are involved, particularly for disorders related to excessive acid secretion, altered bowel motility and obstructive spastic disorders of the respiratory tract without showing any effect on heart rate. The following assay shows that the compounds according to the invention have favourable characteristics in this respect.

PHARMACOLOGY

Antimuscarinic activity and selectivity

Antimuscarinic activity and selectivity were examined in vitro by receptor binding studies in two tissues endowed with $M_1$ and $M_2$ muscarinic receptors (cerebral cortex, heart).

Receptor binding studies in vitro

Muscarinic $M_1$ activity was determined by studying the displacement of ³H-pirenzepine from cerebral cortex homogenate according to the procedure reported below:

The cerebral cortex donors were male CD-COOBBS rats, 220–250 g body weight. The homogenization process was carried out in a Potter-Evelhjem apparatus in the presence of $Na^+/Mg^{++}$ HEPES buffer; pH 7.4 (100 mM NaCl, 10 mM MgCl₂, 20 mM HEPES); by filtering the suspension through two layers of cheesecloth.

Binding curves for the under study compounds were derived indirectly from competition experiments against 0.5 nM ³H-pirenzepine labelling the muscarinic receptors of the cerebral cortex. 1 ml of the homogenate was incubated for 45 min at 30° C. in the presence of a maker ligand and different concentration of the cold ligand, conditions under which equilibrium was reached as determined by appropriate association experiments. The incubation was terminated by centrifugation (12,000 rpm for 3 min) at 200 m temperature using an Eppendorf microcentrifuge. The resultant pellet was washed twice with 1.5 ml saline to remove the free radioactivity and it was allowed to dry. The tips of the tubes containing the pellet were cut off and 200 μl of tissue solubilizer (Lumasolve, Lumac) were added and left to stand overnight. Radioactivity was then counted after addition of 4 ml of liquid scintillation mixture (Dimilume/Toluene 1+10 v:v, Packard).

Assay were carried out in triplicate or quadruplicate and the non-specific binding was defined as the radioactivity bound or entrapped in the pellet when the incubation medium contained 1 μM atropine sulphate. Non-specific binding averaged less than 30%.

$K_D$ values (dissociation constants) were obtained by non-linear regression analysis on the basis of one binding site model with TOPFIT-pharmacokinetic programme package (G. Heinzel "Pharmacokinetics During Drug Development: Data Analysis and Evaluation Techniques" Eds. G. Bolzer and J. M. Van Rossum; p. 207, G. Fisher, New York, 1982) after correction for the radioligand occupancy shift according to the equation: $K_D = IC_{50}/1 + {}^*C/{}^*K_D$, where ${}^*C$ and ${}^*K_D$ represent the concentration and the dissociation constants of the radioligand, used respectively.

Muscarinic $M_2$ activity was examined by studing the displacement of $^3H$-NMS from total heart homogenate according to a procedure identical to the one already described hereinbefore for the muscarinic $M_1$ activity. The results are reported in the following table I:

TABLE I

| Muscarinic Receptor binding studies $K_D$ (nM) | | |
|---|---|---|
| Compound | $M_1$ (Cortex) | $M_2$ (Heart) |
| 1 | 50 | 1870 |
| 2 | 2.9 | 57 |
| 3 | 48 | 800 |
| 4 | 3 | 40 |
| 5 | 25 | 530 |
| 6 | 4.4 | 133 |
| 7 | 90 | 1130 |
| 8 | 60 | 3470 |
| 9 | 50 | 930 |
| 11 | 11 | 120 |
| 12 | 2 | 89 |
| 16 | 30 | 800 |
| 19 | 13 | 450 |
| 20 | 13 | 480 |

According to a further feature of the present invention there are provided pharmaceutical compositions comprising as active ingredient at least one compound of formula (I), as hereinbefore defined, or a physiologically acceptable acid addition salt thereof in association with one or more pharmaceutical carriers, diluents or excipients. For pharmaceutical administration the compounds of general formula (I) and their physiologically acceptable acid addition salts may be incorporated into the conventional pharmaceutical preparations in either solid or liquid form. The compositions may, for example, be presented in a form suitable for oral, rectal or parenteral administration. Preferred forms include, for example, capsules, tablets, coated tablets, ampoules, suppositories and oral drops.

The active ingredient may be incorporated in excipients or carriers conventionally used in pharmaceutical compositions such as, for example, talc, arabic gum, lactose, gelatine, magnesium stearate, corn starch, aqueous or non-aqueous vehicles, polyvinylpyrrolidone, semisynthetic glycerides of fatty acids, sorbitol, propylene glycol, citric acid, sodium citrate.

The compositions are advantageously formulated in dosage units, each dosage unit being adapted to supply a single dose of the active ingredient. Each dosage unit may conveniently contain from 0.01 mg to 100 mg and preferably from 0.05 mg to 50 mg.

The following examples illustrate some of the new compounds according to the present invention, but they are not considered in any way limitative of the scope of the invention itself:

EXAMPLE 1

Piperidine-2-oxo-6-phenyl-6-ethyl carboxylate a) A suspension of α-phenyl-glycine methyl ester (6.3 g), benzaldehyde (4.05 g) and $MgSO_4$ (20 g) in $CH_2Cl_2$ (80 ml) was stirred for 48 hours at room temperature. The reaction mixture was filtered and evaporated to dryness under vacuum. From the crude residue, after distillation (b.p. 166°–164° C., 0.05 mmkg) 6.8 g of the pure intermediate N-benzyliden-α-phenyl-glycine methyl ester were obtained.

b) 4-bromo-ethyl butirrate (6.1 g) was slowly dropped into a well stirred solution of the above Shiff base intermediate (7.2 g) and 80% NaH in anhydrous DMF. The temperature was kept under 30° C. during stirring overnight; then the reaction mixture was poured in ice-water. The oily phase was extracted several times into diethyl ether; the combined organic extracts were washed with water, dried over $MgSO_4$ and evaporated to dryness.

c) The above obtained intermediate was dissolved in 10% HCl and stirred for one hour; the aqueous solution was adjusted at pH 7.5 with 10% NaOH and extracted with ethyl acetate. The organic extracts were washed with water, dried over $MgSO_4$, filtered and evaporated to dryness. From the crude residue, after crystallization from light petrol ether, the pure title compound was obtained. 2.8 g. M.p. 122°–124° C.

MS (C.I.) = 248 m/e [M+H]

EXAMPLE 2

Piperidine-2-oxo-3-cyclohexyl-3-ethyl carboxylate

A solution of diethyl-(2-cyano-ethyl)-phenyl malonate (72.5 g) in ethanol (720 ml) was hydrogenated in a Parr shaker at room temperature and 40 psi pressure over platinum dioxide (7 g) in the presence of 17% hydrochloric acid in ethanol (160 ml). When the theoretical amount of hydrogen had been absorbed, the catalyst was removed by filtration and the solution was evaporated to dryness. The crude residue was taken up into ethylacetate; this solution was washed first with a 17% $Na_2CO_3$ solution, afterwards with water and then dried over $Na_2SO_4$. After evaporation of the ethyl acetate, the pure title compound was obtained by crystallization from diethyl ether. 36.5 g. M.p. 85°–87° C.

MS (C.I.) = 254 m/e [M+H]

EXAMPLE 3

Piperidine-2-oxo-3-cyclohexyl-3-potassium carboxylate

A solution of piperidine-2-oxo-3-cyclohexyl-3-ethyl carboxylate (14.5 g) and 85% KOH (7.5 g) in 95% ethanol (55 ml) was stirred at room temperature overnight. The separated potassium salt was filtered and dried. 8.6 g. M.p. 140°–145° C. (dec.).

M.S. (C.I.) = 276 m/e [M+H]

EXAMPLE 4

Piperidine-2-oxo-4-phenyl-4-ethyl carboxylate a) A solution of acetyl chloride (6.3 g) in benzene (40 ml) was dropped into a well stirred suspension of 4-phenyl-4-carbethoxy piperidine (17 g) and $Na_2CO_3$ (7.8 g) in benzene (190 ml) and water (115 ml). After two hours stirring the organic layer was separated, washed with water several times and dried. From the benzene solution after evaporation to dryness and crystallization from light petrol ether 4-phenyl-4-carbethoxy-1-acetyl piperidine was obtained as a white solid. 18.5 g. M.p. 84°–85° C.

b) The above obtained intermediate (16.5 g) was dissolved into ethyl-acetate (225 ml) and 10% $NaJO_4$ aqueous solution (585 ml) was added. The two phase suspension was stirred for three days at room temperature in the presence of Rhutenium (IV) oxide hydrate (260 mg). The organic layer was separated, washed with an aqueous solution of sodium bisulfite, with water and dried over $MgSO_4$. From the evaporated solution, the pure intermediate 4-phenyl-4-carbethoxy-2-oxo-1-acetyl piperidine was obtained, after crystallization from light petrol ether, as a white solid. 10.8 g. M.p. 45°–46° C.

c) The above described compound (9 g) was dissolved in THF (90 ml) and stirred for five days at room temperature in the presence of few drops of 10% HCl. The solution was evaporated to dryness and the residue was partitioned between water and ethyl acetate. From the dried and evaporated solution of ethyl acetate the title compound was obtained as a white solid in a pure form after crystallization from diethyl ether. 6.7 g. M.p. 137°–138° C.

MS (C.I.)=248 m/e [M+H]

EXAMPLE 5

2,6-Dioxo-3-phenyl-3-carbetoxy piperidine

A solution of 2-cyano-2-phenyl-diethyl glutarrate (14.6 g) in glacial acetic acid (24 ml) and sulphuric acid (24 ml) was heated at 100° C. for 30 minutes. The reaction mixture was cooled and poured on ice and water. The white solid which separated was filtered, washed with water and dried to give the pure title compound. 10 g. M.p. 135°–138° C. (dec.).

MS (C.I.)=262 m/e [M+H]

EXAMPLE 6

Piperidine-1-methyl-2-oxo-3-phenyl-3-ethyl carboxylate

A solution of 2-oxo-3-phenyl-3-ethyl carboxylate-piperidine (4 g) in anhydrous THF (40 ml) was dropped into a cooled suspension of 80% NaH (0.6 g) in anhydrous THF (4 ml). After 30 minutes stirring, methyl iodide (2.3 g) was introduced into the reaction mixture at room temperature and stirring was kept overnight. The mixture was evaporated to dryness, the residue partitioned between water and ethylacetate; the organic layer was dried and evaporated. The intermediate title compound was obtained in a pure form after column chromatography (eluent: 97-3, $CH_2Cl_2$-ethanol). 2.6 g. M.p. 92°–93° C.

MS (C.I.)=250 m/e [M+H]

EXAMPLE 7

Pyrrolidine-2-oxo-4-phenyl-4-ethyl carboxylate a) Ethyl phenyl cyano acetate (25 g) was added to a cooled, stirred solution of sodium (3 g) in ethanol (85 ml). The mixture was stirred for 1 hour, then treated with 2-bromo ethyl acetate (22 g) dropwise. The reaction mixture was stirred overnight at room temperature; cooled, filtered and concentrated. The oily residue was purified by distillation to give 2-cyano-2-phenyl-diethyl-succinate. 17.2 g. B.p. 131°–134° C. (0.3 mm Hg).

b) The above described intermediate (7.6 g) dissolved into EtOH (75 ml) was hydrogenated at room temperature and at atmospheric pressure in the presence of Raney Nickel (0.6 g). When the theoretical amount of hydrogen was taken up, the mixture was filtered and evaporated to dryness. The oily residue was left two days under a 1-1 mixture of diethyl ether and light petrol ether. The pure title compound was obtained as a white solid. 2.8 g. M.p. 108°–110° C.

MS (C.I.)=234 m/e [M+H]

EXAMPLE 8

Pyrrolidine-2-oxo-5-phenyl-5-ethyl carboxylate a) A suspension of 2-phenyl-2-cyano-diethyl glutarrate (80 g) in concentrated $H_2SO_4$ (180 ml) and water (7.5 ml) was stirred at room temperature overnight; the suspension was then diluted with water and ice and extracted into ethyl acetate. The organic solution was washed with water, dried and evaporated to dryness. 2-Phenyl-2-carbamyl-diethyl glutarrate was obtained as a white solid after trituration with petrol ether. 42 g. M.p. 78°–79° C.

b) The above described intermediate (4.2 g) was added portionwise to a solution of bis(trifluoroacetoxy)iodo benzene (7.2 g) in acetonitrile (18 ml) and water (18 ml). The solution was stirred at room temperature for 90 minutes, then it was diluted with water (220 ml) and concentrated hydrochloric acid solution (22 ml) and stirred further for 2 hours. The aqueous acid solution was washed with light petrol ether and neutralized with 17% $Na_2CO_3$ solution. The oil, which separated was extracted into ethyl acetate and washed with water. The organic solution was evaporated to dryness to leave a thick oil from which the title compound was obtained as a white solid upon standing for several days. 0.85 g.

MS (C.I.)=234 m/e [M+H]

EXAMPLE 9

Azepine-2-oxo-6-phenyl-6-ethyl carboxylate a) Ethyl phenyl cyano acetate (56.7 g) was dropped into a cooled solution of Na (6.9 g) in absolute ethanol (200 ml). After 30 minutes stirring 4-bromo-ethyl butyrate (58.5 g) was added, keeping the temperature between 15° and 20° C. The reaction mixture was stirred overnight at room temperature, then it was evaporated to dryness.

The residue was partitioned between diethyl ether and water, the organic solution was washed with diluted hydrochloric acid and water, then was dried. After evaporation to dryness, from the crude residue the intermediate 2-cyano-2-phenyl-diethyl adipate was obtained after distillation. 79 g. B.p. 152°–155° C. (0.06 mmHg.)

b) A solution of the above described intermediate (20 g) in absolute ethanol (200 ml) and 30% hydrochloric acid in ethanol (23 ml) was hydrogenated at room temperature and pressure in the presence of C/Pd as a catalyst (6.5 g). When the theoretical amount of hydrogen was taken up, the catalyst was filtered and the solution evaporated to dryness. The residue was dissolved in water, and washed with diethyl ether. From the aqueous solution, after neutralization with 5% NaOH solution and extraction with ethyl acetate of the oil which separated, the title compound was obtained as a white solid. 7.2 g. M.p. 140°–142° C.

MS (C.I.)=262 m/e [M+H]

EXAMPLE 10

Piperidine-2-thioxo-3-phenyl-3-ethyl carboxylate

A suspension of piperidine-2-oxo-3-phenyl-3-ethyl carboxylate (10 g) and phosphorus pentasulfide (2.6 g) in toluene (600 ml) was heated at 100° C. for 6 hours. The cooled solution was washed with diluted hydrochloric acid and water and then evaporated to dryness. The title compound was obtained as a yellow solid after crystallization of the crude residue from diethyl ether. 6.4 g. M.p. 151°-152° C.

MS (C.I.)=264 m/e [M+H]

EXAMPLE 11

Piperidine-2-oxo-3-(thiophen-2-yl)-3-ethyl carboxylate a) 2-(Thiophen-2-yl)-diethyl malonate (32 g) was slowly added to a solution of Na (3.65 g) in absolute ethanol (160 ml) at a temperature of 45° C. After 30 min. stirring, the reaction mixture was cooled at room temperature and a solution of 1,3-dibromopropane (34.7 g) in toluene was added. The resulting suspension was heated at 110° C. for 4 hours, cooled at room temperature and washed with water. The organic solution was evaporated to dryness; the crude oily residue was distilled to give 18.2 g of 2-(thiophen-2-yl)-2-(3-bromopropyl)-diethyl malonate. B.p. 145°-155° C., 0,02 mm Hg.

b) A solution of this intermediate (10.5 g) sodium azide (3.75 g) and tetrabutylammonium bromide (0.93 g) in benzene (80 ml) and DMF (120 ml) was heated at 100° C. for 4 hours. The reaction mixture was cooled and poured in cold water. The intermediate azide derivative which separated, was quickly extracted into benzene and allowed to react with triethylphosphite (6 ml) at room temperature. After 5 hours stirring gaseous hydrochloric acid was introduced into the reaction mixture for 2 hours. The suspension was then evaporated to dryness and the residue was portioned between diethylether and 10% NaOH aqueous solution. The organic layer was separated and evaporated to dryness. The pure title compound was obtained from the crude residue after crystallization from diisopropyl ether, as a white solid. 5.75 g. M.g. 102°-103° C.

MS (C.I.)=254 m/e [M+H]

EXAMPLE 12

Piperidine-2-oxo-5-(pyridin-2-yl)-5-ethyl carboxylate a) Ethyl-(2-pyridyl)-cyanoacetate (16.4 g) was added to a stirred solution of sodium (1.98 g) in ethanol (65 ml). After 1 hour stirring at room temperature, ethyl 3-bromopropionate (15.6 g) was added. The mixture was stirred overnight, cooled, filtered and evaporated to dryness. The residue was eluted over silicagel (toluene-ethyl acetate 8:2 as eluent) to give diethyl 2-cyano-2-(2-pyridyl)glutarrate (11.6 g) as a thick oil.

b) A solution of the above described compound (5 g) in ethanol (55 ml) was hydrogenated at room temperature and atmospheric pressure over Raney Nickel (0.5 g). When the theoretical amount of hydrogen was absorbed, the reaction mixture was filtered and evaporated to dryness. The residue was purified by elution with methylene chloride-methanol 95:5 on silicagel to give 3.64 g of the title compound as a colourless oil.

MS (C.I.)=249 m/e [M+H]

EXAMPLE 13

Piperidine-1-acetyl-3-phenyl-3-ethyl carboxylate

To a mixture of 3-phenyl-piperidin-3-carboxylic acid ethyl ester (6.8 g) in benzene (75 ml) and sodium carbonate (3.1 g) in water (45 ml), a solution of acetyl chloride (2.52 g) in benzene (20 ml) was added under stirring. The reaction was stirred overnight at room temperature, then the organic layer was washed with water, dried and evaporated to dryness to give 7.98 g of the title compound as a thick oil.

MS (C.I.)=276 m/e [M+H]

EXAMPLE 14

Piperidine-2-oxo-4-phenyl-4-[(R)-1-azabicyclo(2.2.2)octyl]-carboxylate (Compound 1)

A solution of 2-oxo-4-phenyl-4-piperidincarboxylic acid (1.09 g) and 1.1-carbonyl diimidazole (0.81 g) in anhydrous DMF (12 ml) was dropped into a well stirred solution of R(-)-3-quinuclidinol (0.64 g) and 80% NaH (0.15 g) in anhydrous DMF. The reaction mixture was stirred overnight at room temperature, then DMF was removed in vacuo. The residue was partitioned between water and ethylacetate; the organic layer was washed with water, dried over $Na_2SO_4$, filtered and evaporated to dryness. The residue was chromatographated on silicagel (eluent: 90-10-1, $CH_2Cl_2$—MetOH—$NH_4OH$; Rf 0.3). The title compound was obtained as a 1:1 diastereoisomeric mixture. 0.72 g. M.p. 177°-179° C. (from diethyl ether).

MS (C.I.)=329 m/e [M+H]

HPLC: Diaster. A, tr 6.11. Diaster. B, tr 6.73. [Supelcosil LC8 column, eluents: $CH_3CN$ 60-$H_3CO_4$/$Net_3$ 40; T=40° C.]

| Analysis | | | | | | | |
|---|---|---|---|---|---|---|---|
| $C_{19}H_{24}N_2O_3$ | Found % | C | 69.41 | H | 7.40 | N | 8.49 |
| | Calc. % | C | 69.49 | H | 7.37 | N | 8.53 |

Following the above described procedure the following compound has been prepared:

Pyrrolidine-2-oxo-4-phenyl-4-[(R)-1-azabicyclo(2.2.2)octyl]-carboxylate (Compound 2)

M.p. 90°-94° C. (dec.) (from diethyl ether)
MS (C.I.)=315 m/e [M+H]
HPLC: Diaster. A, tr 8.67. Diaster. B, tr 9.08. [Nucleosil C8 column, eluents $CH_3CN$ 15-$H_3PO_4$/$NEt_3$ 40-$H_2O$ 45; T=40° C.]

| Analysis | | | | | | | |
|---|---|---|---|---|---|---|---|
| $C_{18}H_{22}N_2O_3$ | Found % | C | 68.71 | H | 7.12 | N | 8.90 |
| | Calc. % | C | 68.77 | H | 7.05 | N | 8.91 |

EXAMPLE 15

Pyrrolidine-2-oxo-3-phenyl-3-[(R)-1-azabicyclo(2.2.2)-octyl]carboxylate (Compound 3)

(R)(—)-3-quinuclidinol (1 g) was dissolved in benzene (50 ml) and refluxed for 30 minutes using a Dean-Stark reflux head to remouve traces of water. Clean pieces of Na metal (0.18 g) were added and the suspension was refluxed for 60 minutes. Pyrrolidine-2-oxo-3-phenyl-3-ethyl carboxylate (1.6 g), dissolved in dry benzene (20 ml), was added and the reaction mixture was refluxed for six hours. The cooled solution was evaporated to dryness under vacuum, the residue was taken up in ethyl acetate and water and washed with water. The organic layer was dried over $Na_2SO_4$, evaporated to dryness to give a pale yellow residue. This was chromatographated on silicagel (eluents: 90-10-1, $CH_2Cl_2$—MetOH—$NH_4OH$, Rf 0.27) to give the pure title compound as a 1:1 diastereoisomeric mixture. 0.64 g. M.p. 142°–143° C.

MS (C.I.)=315 m/e [M+H]

HPLC: Diaster. A, tr 9.25. Diaster. B, tr 11.42. [Supelcosil LC8 column, eluents: $CH_3CN$ 15-$H_3PO_4$/$NEt_3$ 50-$H_2O$ 35; T=40° C.]

| | Analysis | | | | | | | |
|---|---|---|---|---|---|---|---|---|
| $C_{18}H_{22}N_2O_3$ | Found % | C | 68.70 | H | 7.21 | N | 8.83 |
| | Calc. % | C | 68.77 | H | 7.05 | N | 8.91 |

According to the above described procedure, the following compounds can be prepared:

Piperidine-2.6-dioxo-3-phenyl-3-[(R)-1-azabicyclo(2.2.2)-octyl]-carboxylate (Compound 4)

M.p. 160°–163° C.

MS (C.I.)=343 m/e [M+H]

HPLC: Diaster A, tr 8.63. Diaster B, tr 9.04. [Supelcosil LC8 column, eluents: $CH_3CH$ 40-$H_3PO_4$/$NEt_3$ 40-$H_2O$ 20; T=40° C.]

| | Analysis | | | | | | | |
|---|---|---|---|---|---|---|---|---|
| $C_{19}H_{22}N_2O_4$ | Found % | C | 66.57 | H | 6.51 | N | 8.22 |
| | Calc. % | C | 66.65 | H | 6.48 | N | 8.18 |

Piperidine-2-oxo-6-phenyl-6-[(R)-1-azabicyclo(2.2.2)-octyl]-carboxylate (Compound 5)

M.p. 144°–150° C. (dec.) (as hydrochloride salt, from diethyl ether)

MS (C.I.)=329 m/e [M+H]

HPLC: Diaster A, tr 22.40. Diaster. B, tr 24.06. [DNB-leu column, eluents: n-$C_6H_{14}$ 88-i-PrOH 10-$CH_3OH$ 2; T=25° C.]

| | Analysis | | | | | | | |
|---|---|---|---|---|---|---|---|---|
| $C_{19}H_{25}ClN_2O_3$ | Found % | C | 62.28 | H | 6.99 | N | 7.60 |
| | Calc. % | C | 62.54 | H | 6.91 | N | 7.68 |

Pyrrolidine-2-oxo-5-phenyl-5-[(R)-1-azabicyclo(2.2.2)-octyl]-carboxylate (Compound 6)

M.p. 125°–127° C. (dec.) (as hydrochloride salt from diethyl ether)

MS (C.I.)=315 m/e [M+H]

HPLC: Diaster. A, tr 4.40. Diaster. B, tr 4.90. [Supelcosil LC8DB column, eluents: $CH_3CN$ 30-$H_3PO_4$ (0.01M+0.02% $NEt_3$, pH=3) 40-$H_2O$ 30; T=40° C.]

| | Analysis | | | | | | | |
|---|---|---|---|---|---|---|---|---|
| $C_{18}H_{23}ClN_2O_3$ | Found % | C | 61.03 | H | 6.70 | N | 7.82 |
| | Calc. % | C | 61.62 | H | 6.61 | N | 7.98 |

Piperidine-1-acetyl-3-phenyl-3[(R)-1-azabicyclo(2.2.2)-octyl]-carboxylate (Compound 7)

Thick oil

MS (C.I.)=357 m/e [M+H]

HPLC: Diaster. A, tr 4.45. Diaster. B, tr 4.77. [Nucleosil C8 column, eluents: $CH_3CN$ 40-$H_3PO_4$ 40-$H_2O$ 20; T=40° C.]

| | Analysis | | | | | | | |
|---|---|---|---|---|---|---|---|---|
| $C_{21}H_{28}N_2O_3$ | Found % | C | 70.50 | H | 7.97 | N | 7.72 |
| | Calc. % | C | 70.76 | H | 7.92 | N | 7.86 |

Piperidine-2-oxo-5-(pyridin-2-yl)-5-[(R)-1-azabicyclo(2.2.2)-octyl]-carboxylate (Compound 8)

M.p. 160°–163° C.

MS (C.I.)=330 m/e [M+H]

HPLC: Diaster. A, tr 6.93. Diaster B, tr 7.51. [Nucleosil C8 column, eluents: $CH_3CN$ 10-$H_3PO_4$ 40-water 50; T=40° C.]

| | Analysis | | | | | | | |
|---|---|---|---|---|---|---|---|---|
| $C_{18}H_{23}N_3O_3$ | Found % | C | 65.48 | H | 7.06 | N | 12.69 |
| | Calc. % | C | 65.63 | H | 7.04 | N | 12.76 |

Piperidine-2-thioxo-3-phenyl-3-[(R)-1-azabicyclo(2.2.2)-octyl]-carboxylate (Compound 9)

M.p. 111°–113° C.

MS (C.I.)=345 m/e [M+H]

HPLC: Diaster. A, tr 15.70. Diaster. B, tr 18.00. [DNB Leu column, eluents: n-$C_6H_{14}$ 85-$CH_3OH$ 7-i-PrOH 8; T=25° C.]

| | Analysis | | | | | | | |
|---|---|---|---|---|---|---|---|---|
| $C_{19}H_{24}N_2O_2S$ | Found % | C | 65.88 | H | 6.95 | N | 8.00 |
| | Calc. % | C | 66.24 | H | 7.02 | N | 8.13 |

Piperidine-2-oxo-3-(thiophen-2-yl)-3-[(R)-1-azabicyclo(2.2.2)-octyl]-carboxylate (Compound 10)

M.p. 132° C.

MS (C.I.)=335 m/e [M+H]

HPLC: Diaster. A, tr 20.40. Diaster B, tr 22.00. [DNB Leu column, eluents: n-$C_6H_{14}$ 88-$CH_3OH$ 6-i-PrOH 6. T=30° C.]

| | Analysis | | | | | | | |
|---|---|---|---|---|---|---|---|---|
| $C_{17}H_{22}N_2O_3S$ | Found % | C | 60.45 | H | 6.67 | N | 8.17 |
| | Calc. % | C | 61.05 | H | 6.63 | N | 8.38 |

Piperidine-2-oxo-3-phenyl-3-[(R)-1-azabicyclo(2.2.2)-octyl]-carboxylate (Compound 19)

M.p. 153°–156° C. (from light petrol ether).

MS (C.I.)=329 m/e [M+H]

HPLC: Diaster. A, tr 14,8. Diaster B, tr 16.5. [DNB Leu column, eluents: n-$C_6H_{14}$ 88-i-PrOH 6. $CH_3OH$ 6; T=25° C.]

| | Analysis | | | | | | | |
|---|---|---|---|---|---|---|---|---|
| $C_{19}H_{24}N_2O_3$ | Found % | C | 69.61 | H | 7.41 | N | 8.44 |

| Analysis | | | | | | | |
|---|---|---|---|---|---|---|---|
| | Calc. % | C | 69.49 | H | 7.37 | N | 8.53 |

Piperidine-2-oxo-5-phenyl-5-[(R)-1-azabicyclo(2.2.2)-octyl]-carboxylate (Compound 20)

M.p. 181°–184° C. (from light petrol ether).
MS (C.I.)=329 m/e [M+H]
HPLC: Diaster. A, tr 9,6. Diaster B, tr 11.1. [Supelcosil LC8 column, eluents: $CH_3CN$ 15-$H_3PO_4$/$NEt_3$ (pH3) 50-$H_2O$ 35; T=40° C.]

| Analysis | | | | | | | |
|---|---|---|---|---|---|---|---|
| $C_{19}H_{24}N_2O_3$ | Found % | C | 69.80 | H | 7.30 | N | 8.46 |
| | Calc. % | C | 69.49 | H | 7.37 | N | 8.53 |

EXAMPLE 16

Azepine-2-oxo-6-phenyl-6-[(R)-1-azabicyclo(2.2.2)-octyl]-carboxylate (Single diastereoisomer, compound 11) and Azepine-2-oxo-6-phenyl-6-[(R)-1-azabicyclo(2.2.2)-octyl]-carboxylate (Single diastereoisomer, compound 12)

A suspension of R(-)-3-quinuclidinol (0.95 g) and Na (0.17 g) in anhydrous THF was refluxed for 30 minutes, then it was cooled.

A solution of azepine-2-oxo-6-phenyl-6-ethyl carboxylate (1.6 g) and 1,1-carbonyl diimidazole (1.1 g) in anydrous THF (30 ml) was then introduced, and the resulting reaction mixture was refluxed for 4 hours. After cooling, a few drops of glacial acetic acid were added dropwise and the reaction mixture was evaporated to dryness. Flash chromatography on silicagel (eluent $CH_2Cl_2$—MetOH—$NH_4OH$ 95:5:0.5) separated the 1:1 pair of diastereoisomers into a clean upper (Rf 0.3) and a clean lower (Rf 0.25) component. Each component was evaporated to dryness to give the single separated diastereoisomer as white solid (after trituration with diethyl ether).

Azepine-2-oxo-6-phenyl-6[(R)-1-azabicyclo(2.2.2)-octyl]-carboxylate (Upper component, compound 11)

M.p. 171°–175° C. (dec.) (from diethyl ether)
MS (C.I.)=343 m/e [M+H]
HPLC: tr 4.78. [Supelcosil LC8 column, eluents: $CH_3CN$ 30-$H_3PO_4$/$NEt_3$ 40-$H_2O$ 30; T=40° C.]

| Analysis | | | | | | | |
|---|---|---|---|---|---|---|---|
| $C_{20}H_{26}N_2O_3$ | Found % | C | 70.01 | H | 7.67 | N | 8.24 |
| | Calc. % | C | 70.15 | H | 7.65 | N | 8.18 |

Azepine-2-oxo-6-phenyl-6-[(R)-1-azabicyclo(2.2.2)-octyl]-carboxylate (lower component, compound 12)

M.p. 156°–159° C. dec. (from diethyl ether)
MS (C.I.)=343 m/e [M+H]
HPLC: tr 5.63. [Supelcosil LC8 column, eluents: $CH_3CN$ 30-$H_3PO_4$/$NEt_3$ 40-$H_2O$ 30; T=40° C.]

| Analysis | | | | | | | |
|---|---|---|---|---|---|---|---|
| $C_{20}H_{26}N_2O_3$ | Found % | C | 70.24 | H | 7.61 | N | 8.22 |

| Analysis | | | | | | | |
|---|---|---|---|---|---|---|---|
| | Calc. % | C | 70.15 | H | 7.65 | N | 8.18 |

EXAMPLE 17

Piperidine-1-methyl-2-oxo-3-phenyl-3-[(R)-1-azabicyclo(2.2.2)-octyl]-carboxylate (Compound 13)

Sodium (0.4 g) and methanol (7 ml) were introduced into anhydrous heptane (400 ml). When all Na was dissolved, excess methanol was distilled off and R(-)-3-quinuclidinol (2.54 g) and piperidine-1-methyl-2-oxo-3-phenyl-3-ethyl carboxylate (4.98 g) were added. The reaction mixture was heated and the solvent was distilled during 3 hours (about 300 ml). After cooling 2N hydrochloric acid (40 ml) was dropped in, and from the separated aqueous layer, after neutralization with 10% NaOH, extraction into ethyl acetate and evaporation, the crude title compound was obtained as a clear oil. This was purified by column chromatography (eluent: $CH_2Cl_2$—MetOH—$NH_4OH$ 90:10:1). 2.8 g. M.p. 58°–64° C. (dec.) (as lyophilized hydrochloride salt).

MS (C.I.)=343 m/e [M+H]
HPLC: Diaster. A, tr 13.53. Diaster. B, tr 14.76. [DNB-leu column, eluents: n-$C_6H_{14}$ 90-i-PrOH 4-$CH_3OH$ 6; T=25° C.]

| Analysis | | | | | | | |
|---|---|---|---|---|---|---|---|
| $C_{20}H_{27}ClN_2O_3$ | Found % | C | 63.20 | H | 7.22 | N | 7.29 |
| | Calc. % | C | 63.39 | H | 7.18 | N | 7.39 |

EXAMPLE 18

Piperidine-2-oxo-3-cyclohexyl-3-[(R)-1-azabicyclo(2.2.2)-octyl]-carboxylate (Compound 14)

Piperidine-2-oxo-3-cyclohexyl-3-potassium carboxylate (1 g) was added portionwise to a cooled solution of tionyl chloride (10 ml) in anhydrous benzene (10 ml). The suspension was stirred overnight at room temperature and then evaporated to dryness. To this crude residue, suspended in anhydrous THF (20 ml), was added under stirring R(-)-3-quinuclidinol (0.96 g). The reaction mixture was stirred for 4 hours at room temperature and then evaporated to dryness. From this crude residue after porification by column chromatography on silicagel (eluent: $CH_2Cl_2$—MetOH—$NH_4OH$ 90:10:1, Rf 0.22) the pure title compound was isolated as a clear thick oil. 0.6 g. M.p. 58°–62° C. (dec.) (as a lyophilized hydrochloride salt).

MS (C.I.)=335 m/e [M+H]
HPLC: Diaster. A, tr 8.73. Diaster. B, tr 10.28. [DNB-leu column, eluents: n-$C_6H_{14}$ 88-i-PrOH 6-$CH_3OH$ 6; T=25° C.]

| Analysis | | | | | | | |
|---|---|---|---|---|---|---|---|
| $C_{19}H_{31}ClN_2O_3$ | Found % | C | 61.41 | H | 8.50 | N | 7.50 |
| | Calc. % | C | 61.52 | H | 8.42 | N | 7.55 |

EXAMPLE 19

Azepine-2-oxo-6-phenyl-6-[(R)-1-azabicyclo(2.2.2)-octyl]-carboxylate, methyl bromide (Compound 15)

A solution of azepine-2-oxo-6-phenyl-6-[(R)-1-azabicyclo(2.2.2)-octyl]-carboxylate (0.5 g) and methyl bromide (2M solution in diethyl ether) (1.53 ml) in acetonitrile (7 ml) was stirred at room temperature for 2 days. The solution was evaporated to dryness, to give after lyophilization the pure title compound. 0.55 g.

M.p. 60°–68° C. (dec.) (after lyophilization)

HPLC: Single diastereoisomer, tr 3.80 [Supelcosil LC8 column, eluents: $CH_3CN$ 30-$H_3PO_4$ (0.01M+0.02% $NEt_3$, pH 3) 40-$H_2O$ 30; T=40° C.]

| Analysis | | | | | | | |
|---|---|---|---|---|---|---|---|
| $C_{21}H_{29}BrN_2O_3$ | Found % | C | 57.00 | H | 6.89 | N | 6.15 |
| | Calc. % | C | 57.67 | H | 6.68 | N | 6.40 |

Following the above described procedure and utilizing the suitable intermediate, the following compounds can be prepared:

Azepine-2-oxo-6-[(R)-1-azabicyclo(2.2.2)-octyl]-carboxylate, methyl bromide (Single diastereoisomer, compound 16)

M.p. 67°–72° C. (dec.) (after lyophilization)

HPLC: Single diastereoisomer, tr 4.10. [Supelcosil LC8 column, eluents: $CH_3CN$ 40-$H_3PO_4$ (0.01M+0.02% $NEt_3$, pH 3) 40-$H_2O$ 20; T=40° C.]

| Analysis | | | | | | | |
|---|---|---|---|---|---|---|---|
| $C_{21}H_{29}BrN_2O_3$ | Found % | C | 56.85 | H | 6.83 | N | 6.18 |
| | Calc. % | C | 57.67 | H | 6.68 | N | 6.40 |

Piperidine-2-oxo-5-phenyl-5-[(R)-1-azabicyclo(2.2.2)-octyl]-carboxylate, cyclopropylmethyl bromide (Compound 17)

M.p. 65°–70° C. (dec.) (after lyophilization)

HPLC: Diasteroisomeric mixture, tr 10.10. [Supelcosil LC8 column, eluents $CH_3CN$ 20-$H_3PO_4$ (0.01M+0.02% $NEt_3$, pH 3) 60-$H_2O$ 20; T=40° C.]

| Analysis | | | | | | | |
|---|---|---|---|---|---|---|---|
| $C_{23}H_{31}BrN_2O_3$ | Found % | C | 59.48 | H | 6.79 | N | 6.00 |
| | Calc. % | C | 59.61 | H | 6.74 | N | 6.05 |

Piperidine-2-oxo-5-phenyl-5-[(R)-1-azabicyclo(2.2.2)-octyl]-carboxylate, methyl bromide (Compound 18)

M.p. 112° C. (dec.)

HPLC: Diaster. A, tr 8.85. Diaster. B, tr 9.34. [Supelcosil LC8 column, eluents: $CH_3CN$ 15-$H_3PO_4$/$NEt_3$ 50-$H_2O$ 35; T=40° C.]

| Analysis | | | | | | | |
|---|---|---|---|---|---|---|---|
| $C_{20}H_{27}BrN_2O_3$ | Found % | C | 56.80 | H | 6.38 | N | 6.68 |
| | Calc. % | C | 56.74 | H | 6.43 | N | 6.62 |

The following not limitative examples of pharmaceutical compositions according to the present invention are reported:

EXAMPLE 20

| Tablets | |
|---|---|
| active ingredient | 10 mg |
| lactose | 207 mg |
| corn starch | 30 mg |
| magnesium stearate | 3 mg |

Method of preparation: the active ingredient, lactose and corn starch were mixed and homogeneously moistened with water. After screening of the moist mass and drying in a tray drier, the mixture was again passed through a screen and magnesium stearate was added. Then the mixture was pressed into tablets weighing 250 mg each. Each tablet contains 10 mg of the active ingredient.

EXAMPLE 21

| Capsules | |
|---|---|
| active ingredient | 10 mg |
| lactose | 188 mg |
| Magnesium stearate | 2 mg |

Method of preparation: the active ingredient was mixed with the auxiliary products, and the mixture was passed through a screen and mixed homogeneously in a suitable device. The resulting mixture was filled into hard gelatine capsules (200 ml per capsule); each capsule contains 10 mg of active ingredient.

EXAMPLE 22

| Ampoules | |
|---|---|
| active ingredient | 2 mg |
| sodium chloride | 9 mg |

Method of preparation: the active ingredient and sodium chloride were dissolved in an appropriate amount of water for injection. The resulting solution was filtered and filled into vials under sterile conditions.

EXAMPLE 23

| Suppositories | |
|---|---|
| active ingredient | 25 mg |
| semisynthetic glicerides of fatty acids | 1175 mg |

Method of preparation: the semisynthetic glicerides of fatty acids were melted and the active ingredient was added while stirring homogeneously. After cooling at a proper temperature the mass was poured into prefomed moulds for suppositories weighing 1200 mg each. Each suppository contains 25 mg of active ingredient.

EXAMPLE 24

| Oral drops | |
|---|---|
| active ingredients | 5 mg |
| sorbitol | 350 mg |
| propylene glycol | 200 mg |
| citric acid | 1 mg |
| sodium citrate | 3 mg |

| Oral drops | |
|---|---|
| demineralized water q.s. | 1 ml |

Method of preparation: the active ingredient, citric acid and sodium citrate were dissolved in a mixture of a proper amount of water and propylene glycol. Then sorbitol was added and the final solution was filtered. The solution contains 1% of active ingredient and is administered by using a proper dropper.

What is claimed is:

1. A compound of the formula (I)

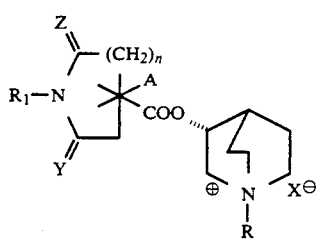

wherein

R represents a linear or branched $C_{1-3}$alkyl group, a $C_{5-7}$cycloalkyl-$C_{1-2}$alkyl group, or it is absent;

X represents a chloride, bromide, iodide or $CH_3SO_4$ ion, or it is absent when R is absent;

$R_1$ represents H, a linear or branched $C_{1-3}$alkyl group or an acyl group of the type $R_2$-CO, in which $R_2$ is H or a linear or branched $C_{1-3}$alkyl group;

A represents $C_{5-7}$cycloalkyl, phenyl, thieno, pyridino or piperidino;

Y and Z may be simultaneously or alternatively present or absent; when they are simultaneously present, they represent oxygen; when only one of them is present, it is oxygen or sulfur;

n is 1, 2 or 3; and

A and the 3-quinuclidinyl ester group are attached to the same carbon atom of the ring;

or a pharmaceutically acceptable acid addition salt of such compound wherein R and X are absent.

2. A compound of formula (I) according to claim 1, wherein $R_1$ is H, Z is oxygen or sulfur, n is 1, 2 or 3 and A is a phenyl or thiophene ring, R is absent or it is a linear or branched $C_{1-3}$alkyl group or a $C_{5-7}$cycloalkyl-$C_{1-2}$alkyl group, and X is absent or it is a bromide ion.

3. A pharmaceutically acceptable salt of a compound of formula I, in accordance with claim 1, selected from the group consisting of salts formed by reaction of a compound of formula I with hydrochloric, hydrobromic, sulfuric, methanesulfonic or tartaric acid.

4. A compound selected from the group consisting of:
Piperidine-2,6-dioxo-3-phenyl-3-[(R)-1-azabicyclo(2.2.2)-octyl]-carboxylate;
Piperidine-2-oxo-6-phenyl-6-[(R)-1-azabicyclo(2.2.2)-octyl]-carboxylate;
Pyrrolidine-2-oxo-4-phenyl-4-[(R)-1-azabicyclo(2.2.2)-octyl]-carboxylate;
Pyrrolidine-2-oxo-5-phenyl-5-[(R)-1-azabicyclo(2.2.2)-octyl]-carboxylate;
Azepine-2-oxo-6-phenyl-6-[(R)-1-azabicyclo(2.2.2)-octyl]-carboxylate single diastereoisomer;
Azepine-2-oxo-6-phenyl-6-[(R)-1-azabicyclo(2.2.2)-octyl]-carboxylate single diastereoisomer;
Piperidine-2-oxo-3-phenyl-3-[(R)-1-azabicyclo(2.2.2)-octyl]-carboxylate; and,
Piperidine-2-oxo-5-phenyl-5-[(R)-1-azabicyclo(2.2.2)-octyl]-carboxylate.

5. A pharmaceutical composition suitable for use in the treatment of patients suffering from peptic ulcer disease, irritable bowel syndrome, spastic constipation, cardiospasm or pylorospasm, obstructive acute or chronic spastic disorders of the respiratory tract, spastic disorders of the urinary or biliary tracts or in the treatment of urinary incontinence, comprising a therapeutically effective amount of a compound of formula I, in accordance with claims 1, 2, 3, or 4 and a pharmaceutically acceptable carrier.

6. A method for treating peptic ulcer disease, irritable bowel syndrome, spastic constipation, cardiospasm or pylorospasm which method comprises administering to a warm blooded animal suffering from the same a therapeutically effective amount of a compound of formula I, in accordance with claims 1, 2, 3, or 4.

7. A method for treating obstructive acute or chronic spastic disorders of the respiratory tract which method comprises administering to a warm blooded animal suffering from the same a therapeutically effective amount of a compound of formula I, as set forth in claims 1, 2, 3 or 4.

8. The method of claim 7 wherein the condition to be treated is bronchoconstriction, chronic bronchitis, emphysema or asthma.

9. A method for treating spastic disorders of the urinary or biliary tracts, or urinary incontinence, which method comprises administering to a warm blooded animal suffering from the same a therapeutically effective amount of a compound of formula I, according to claims 1, 2, 3 or 4.

* * * * *